United States Patent [19]

Cody

[11] Patent Number: 5,716,635
[45] Date of Patent: Feb. 10, 1998

[54] PLANTAGO MAJOR TRANSDERMAL PATCH FOR USE IN TREATING A TOBACCO OR NICOTINE HABIT

[75] Inventor: Mary E. Cody, Boonton Township, N.J.

[73] Assignee: M. E. Cody Products, Inc., Boonton Township, N.J.

[21] Appl. No.: 504,014

[22] Filed: Jul. 19, 1995

[51] Int. Cl.⁶ ........................................ A61L 15/16
[52] U.S. Cl. .................. 424/447; 424/195.1; 424/448; 424/449; 514/813
[58] Field of Search ........................ 424/448, 449, 424/447, 195.1; 514/813

[56] References Cited

U.S. PATENT DOCUMENTS

| | | | |
|---|---|---|---|
| 4,284,089 | 8/1981 | Ray | 131/270 |
| 4,716,120 | 12/1987 | Tsay et al. | 424/276.1 |
| 4,821,745 | 4/1989 | Rosen et al. | 131/270 |
| 4,839,174 | 6/1989 | Baker et al. | 424/447 |
| 4,908,213 | 3/1990 | Govil et al. | 424/447 |
| 4,920,989 | 5/1990 | Rose et al. | 131/270 |
| 4,943,435 | 7/1990 | Baker et al. | 424/448 |
| 4,946,853 | 8/1990 | Bannon et al. | 514/343 |
| 4,953,572 | 9/1990 | Rose et al. | 131/270 |
| 4,963,356 | 10/1990 | Calenoff et al. | 424/276.1 |
| 5,016,652 | 5/1991 | Rose et al. | 131/270 |
| 5,135,753 | 8/1992 | Baker et al. | 424/435 |
| 5,162,037 | 11/1992 | Whitson-Fischman | 600/12 |
| 5,192,542 | 3/1993 | Hubbs et al. | 424/195.1 |

OTHER PUBLICATIONS

Clinical Study, An Open Label Evaluation of the Tobacco Aversion Caused by Plantago Major Tincture in Subjects Who Are Heavy Smokers, Essex Testing Clinic Inc., Verona, NJ pp. 1–22, Constance J. DiFiglia, M.D., 1992.

Oscar E. Boericke, A.B., M.D., Homoeopathic Materia Medica; pp. 521–522, 1953.

Primary Examiner—D. Gabrielle Phelan
Attorney, Agent, or Firm—Fishman, Dionne, Cantor & Colburn

[57] ABSTRACT

A transdermal patch containing an extract of the herb *Plantago major* is presented. Use of the transdermal patch, of the present invention, produces a diminished desire for tobacco (i.e., nicotine) without the use of nicotine itself.

13 Claims, 1 Drawing Sheet

PLANTAGO MAJOR TRANSDERMAL PATCH FOR USE IN TREATING A TOBACCO OR NICOTINE HABIT

BACKGROUND OF THE INVENTION

The present invention relates generally to transdermal patches. More particularly, the present invention relates to a transdermal patch containing as an active ingredient an extract of the herb *Plantago major* for use as an aid in controlling a tobacco (i.e., nicotine) habit.

The U.S. Surgeon General has determined that cigarette smoking is a major risk factor in coronary artery disease and is the cause of approximately 30% of all cancer deaths. Tobacco chewing has been shown to cause cancers of the mouth and throat. Because of the undesirable effects of tobacco smoking or tobacco chewing, many devices have been developed as aids for treatment of the tobacco and nicotine habit. For example, in a simulated smoking device, the tobacco therein is heated rather than burned, releasing nicotine vapor which is then drawn into the smoker's lungs. Thus, the smoker obtains the desired nicotine, but without also ingesting the full range and concentration of harmful products of burning tobacco. One such simulated smoking device using a source of vaporizable nicotine is disclosed in U.S. Pat. No. 4,284,089 issued to Ray. Other simulated smoking devices contain substances which microencapsulate materials that simulate the taste and aroma of tobacco, and which are then released by squeezing or crushing the device. Such devices often do not raise the nicotine level in the blood sufficiently to satisfy the desire for nicotine, and thus are ineffective as aids to stop smoking. Other disadvantages include irritation of the mucosa, which is intolerable to some patients, and the bad taste of nicotine introduced orally.

Alternatively, tobacco concentrates have been processed into tablets or gum which may be sucked or chewed in the mouth of the user, the nicotine being absorbed into the user's body through the lining of the mouth. However, chewing gum formulations suffer from numerous drawbacks. They have a bad taste, they may lead to mouth ulcers and heartburn, they cannot be used effectively by denture wearers, and they depend on the patient following the prescribed chewing regime. Difficulties associated with oral administration of nicotine include nausea, rapid nicotine degradation, and irregular and unpredictable blood plasma levels. Inability to self-administer the gum while the patient is asleep leads to low or even zero levels of nicotine in the morning and a return of the smoking urge. Even with immediate administration of nicotine gum, it can take up to one hour before effective plasma levels of nicotine are again obtained.

Transdermal patches have also been used as aids in the reduction of incidence of tobacco smoking or chewing. These patches contain tobacco or tobacco by-products, as described in U.S. Pat. No. 4,821,745 issued to Rosen et al, or they contain nicotine, as described in U.S. Pat. No. 4,839,174 issued to Baker et al, U.S. Pat. No. 4,908,213 issued to Govil and Kohlman, and U.S. Pat. No. 4,943,435 issued to Baker et al. Patches containing nicotine have been used in conjunction with gum containing nicotine, as described in U.S. Pat. No. 5,135,753 issued to Baker et al, and in conjunction with an oral aerosol spray as described in U.S. Pat. No. 4,920,989, U.S. Pat. No. 4,953,572, and U.S. Pat. No. 5,016,652, all issued to Rose et al.

Transdermal patches are advantageous in that the dosage regime is simplified. A patient using a transdermal patch is less likely to encounter compliance problems than one who is required to swallow pills or chew gum two or more times a day. Another advantage of using a transdermal patch is that delivery of the active agent is steadier and more uniform. In this way, the periodic fluctuations between plasma levels above the necessary threshold and below the efficacy threshold are eliminated. However, nicotine is a known skin irritant, and transdermal patches containing nicotine often cause pruritus.

In addition to the above-described drawbacks and disadvantages, all of these devices and methods suffer from a reliance on nicotine as an aid in controlling nicotine craving, when nicotine is the addictive agent. The use of nicotine as in aid in controlling nicotine addiction can cause addiction to the gum or patch itself. There is also the potential for increased addiction if the patient continues regular use of tobacco while chewing the gum or wearing the patch. Furthermore, nicotine is a known toxin with profound physiological effects on the body, including increasing blood pressure and heart rate.

A metal-based transdermal patch, applied at an acupuncture point in conjunction with a magnetic field, and containing a homeopathic mixture of at least one herb has been disclosed in U.S. Pat. No. 5,162,037 issued to Whitson-Fischman. The patch described therein has several significant features. The patch is made of a porous material such as sintered metal, and is fitted with a metal sphere or ball made of iron, steel or other ferrous alloy. Furthermore, the patch is applied at appropriate acupuncture sites and subjected to a uniform polar magnetic field. The patch is impregnated with a homeopathic mixture of at least one herb, herbal extract or other component such as pineal gland.

Homeopathic mixtures contain minute quantities of compounds that in normal doses cause the same effects as the disease being treated. Thus, a homeopathic mixture calculated to treat nicotine addiction could contain nicotine in minute quantities. The quantities of the therapeutic agent present in a homeopathic mixture are so minute that they are statistically not present. A 1:10 dilution (one part mixture diluted with nine equal parts plain water or alcohol) repeated more than twenty-four times results in a solution with a concentration $1 \times 10^{-24}$th of the original concentration. Statistically, a solution at a concentration $1 \times 10^{-24}$th of the initial concentration can no longer contain the original substance, based on Avogadro's constant. U.S. Pat. No. 5,162,037 further discloses that the homeopathic mixtures are made up of a 1:10 dilution of herbal extract, each dilution being made up to thirty times. Such a dilution results in a solution at a concentration $1 \times 10^{-30}$th of the original concentration, a solution even more dilute than that described above. A solution at a concentration $1 \times 10^{-30}$th of the initial concentration can no longer contain the original substance. Thus, the effective therapeutic concentrations of the herbal mixtures described in this patent are less than zero, or effectively zero.

These homeopathic mixtures contain in addition a magnetically permeable ingredient, preferably ferrous gluconate, $Fe[HOCH_2(CHOH)_4CO_2]_2$, in a non-homeopathic concentration. *Plantago asiaticus* is disclosed as one component of a sixteen-component mixture for use in the treatment of chronic muscular and joint pain.

The herb *Plantago major* has been known as a tobacco deterrent (both smoking tobacco and chewing tobacco) for many years, see Materia Medica, Boericke & Runyan, Boericke & Tafel, Inc. Philadelphia, Pa., 1927, pages 521–522. A clinical trial conducted in 1992 at Essex Testing Clinic in Verona, N.J. also found that oral administration of *Plantago major* extract caused an aversion to tobacco in human subjects who were heavy smokers.

Such tobacco aversion, or a reduction in craving, may be accomplished by oral ingestion of the whole dried herb. However, ingestion can have undesired laxative effects, most likely due to the bulking and mucilage content of the whole herb. Furthermore, oral ingestion of effective amounts of the whole herb may require between twenty and thirty minutes, with dosing up to three to four times a day. Oral dosing in capsule or tablet form presents difficulties for those persons with swallowing disorders. Tinctures and various dilutions in ethanol and water of the herb have also been used orally, generally sublingually or as a food additive. Oral use of tinctures and dilutions can adversely affect the taste of food and alcohol can leave a temporary burning sensation in the user's mouth. Persons who choose to avoid alcohol are not able to use such tinctures.

SUMMARY OF THE INVENTION

The above-discussed and other problems and deficiencies of the prior art are overcome or alleviated by the transdermal patch of the present invention. In accordance with the present invention, a transdermal patch is impregnated with an extract of *Plantago major*. "Transdermal patch" as used herein means any system or device that is attached to the skin of a user and delivers a substance through the intact skin and into the user's body. An important feature of the invention is that the concentration of extract is greater than zero. Provided that the patch maintains essentially continuous contact between the user's skin and the extract, any one or a combination of patch technologies is adaptable for use with *Plantago major* extract. The method of manufacture of the transdermal patch of the present invention depends on the patch technology selected. During use, the patch is placed anywhere on the user's skin that affords convenience and continuous contact between the skin and the *Plantago major* extract.

In contrast to prior art nicotine patches, the present invention uses extracts of the herb *Plantago major*, rather than the toxic alkaloid nicotine as an aid to overcoming nicotine addiction. Indeed, *Plantago major* contains only minuscule quantities of alkaloid compounds, none of which have been documented as the active ingredient for causing a decrease or cessation of the desire to use tobacco. Use of *Plantago major* extract is also expected to result in less skin irritation than is observed with nicotine patches. The patch of the present invention may be used conveniently and privately, and does not require the use of metal patches, magnetically permeable substances, or magnetic fields. In further contrast to the prior art, there are no laxative or other side effects arising from oral ingestion, since such is not required with the present invention.

BRIEF DESCRIPTION OF THE DRAWINGS

The FIGURE is a diagrammatic cross-sectional view of a transdermal patch in accordance with the present invention.

DESCRIPTION OF THE PREFERRED EMBODIMENT

Figure 1:
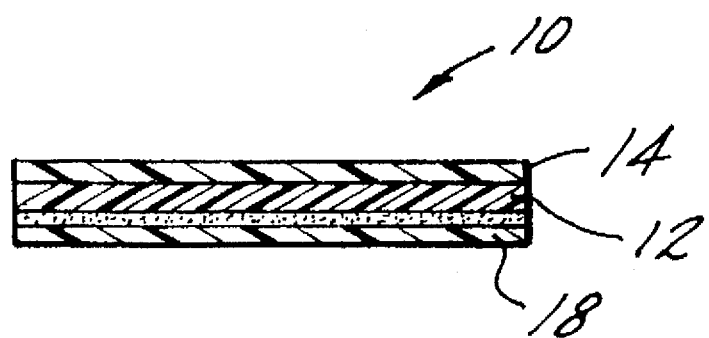

Referring now to the FIGURE, a transdermal patch in accordance with the present invention is generally shown at 10. Transdermal patch 10 comprises a permeable inner layer 12 (i.e., the side closest the skin of the wearer during use) and an impermeable, non-absorbent outer layer 14 (i.e., the side furthest away from the skin of the wearer during use) with a layer 16 of a gel disposed therebetween. Layer 16 is preferably cast onto layer 14 and bonds thereto when cast. Layer 14 is preferably comprised of Teflon-type materials, serves to prevent evaporation from the gel, and protects the gel from being worn away.

Layer 12 is an adhesive layer and serves for attaching patch 10 to a wearer. Adhesive layer 12 is preferably a bioadhesive that has an existing record of use in transdermal devices, e.g., an acrylic- or silicone-based adhesive or polyisobutylene. More preferably, adhesive layer 12 comprises silicone-based adhesives, which do not adversely interact with the gel. Adhesive layer 12 preferably forms a continuous layer which surrounds the gel reservoir. Further, a peel strip or release layer 18 which covers the adhesive layer during storage may be employed. Layer 18 prevents evaporative loss of the gel. Release layer 18 preferably comprises an impermeable film similar to layer 14, alternatively layer 18 is comprised of metal foil, Mylar or any other suitable material known in the art.

The gel comprises an extract of *Plantago major*. It is an important feature of the present invention that the concentration of the extract in the gel is greater than zero. The concentration of the extract in the gel may be from about 1% by volume to about 100% of the total composition. More preferably, the concentration of the extract in the gel is in the range from about 30% to about 90% of the total composition.

The gel preferably comprises water, a gelling agent (e.g., Carbomer), specially denatured alcohol 40, methyldibromoglutaronitrile, phenoxyethanol, *Plantago major* extract, and TEA (i.e., a neutralizer). Alternatively, the gel comprises water, a gelling agent made from a filtered mixture of dried Plantago leaf and water and *Plantago major* extract. In addition, the gel may also include components to aid absorption of the extract through the skin of a wearer, e.g., dimethylsulfoxide (DMSO), $H_3CSOCH_3$.

The above is only exemplary and other prior transdermal patches which are capable of delivering the gel or slurry containing the extract of *Plantago major* may be employed, e.g., transdermal patches described in U.S. Pat. No. 4,821,745 issued to Rosen and Rosen, U.S. Pat. No. 4,839,174 issued to Baker et al., U.S. Pat. No. 4,943,435 issued to Baker et al., U.S. Pat. No. 5,135,753 issued to Baker et al., and U.S. Pat. No. 4,920,989, U.S. Pat. No. 4,953,572, and U.S. Pat. No. 5,016,652, all issued to Rose et al, each of which is incorporated herein by reference in its entirety.

*Plantago major* extract is commercially available from BioBotanica. The tincture used in the present invention is a Class C Tincture. Class C Tinctures are prepared by maceration or percolation from crude botanical substances, fresh or dried, by the dissolving action of an alcoholic vehicle. Class C Tinctures are made to represent one part by weight of dry crude material in ten parts by volume of completed solution. Alternatively, the *Plantago major* extract may be prepared by maceration. Mother tinctures of *Plantago major* are prepared by the maceration (mincing or breaking down) of the fresh material in different strengths of alcohol at ambient (room) temperature. After aging for periods ranging from one hour to one month, the suspension is filtered by gravity or compression. Final alcohol strengths may be 33⅓%, 50% or 80–90%, depending on the water content or the starting material. Succulent, fresh plants yield between 350–700 ml of unfiltered succus (or juice) per kilogram of plant material. The succus is mixed with one half of its volume of 95% pure alcohol (volume/volume), producing mother tinctures of approximately 33⅓% (volume/volume)

alcohol content. Fresh plant material yielding less than 350 ml per kilogram of succus is repeatedly macerated with alcohol/water mixtures, producing mother tinctures of approximately 80–87%(volume/volume) alcohol content. The macerated material is treated with a solution of alcohol (ethanol or ethyl alcohol, and not methanol), and distilled water. The ratio of alcohol to water depends on the relative dryness of the starting material. The extraction dissolves all the therapeutic substances in the starting material. These substances are very often complex and may be thirty or forty in number. The suspension of solid material in the extractant liquid is stored in an amber glass container in a cool, dark place for periods of one hour up to one month. The suspension is filtered to separate the undissolved, solid material from the liquid. Filtration is achieved by gravity, pressure or suction to produce a bright, clear liquid filtrate, which is the mother tincture. The solid material is rejected.

EXAMPLE

The following example demonstrates the preparation of the gel for use with a transdermal patch in accordance with the present invention.

The gel was prepared in accordance with the following steps:

(1) Adding water to a batch (i.e., a vessel);

(2) Creating vortex in the water, by turning on a high speed mixer;

(3) Slowly sprinkling in powder Carbomer (i.e., the gelling agent), so that it completely dissolves;

(4) Continue mixing at room temperature until the powdered polymer has dissolved (e.g., 2–3 hours);

(5) Adding *Plantago major* extract to the batch; and (6) On an equal basis, adding neutralizer (e.g., Triethanolamine/TEA) to the batch to thicken the solution.

During use, the patch is placed in contact with the skin so that the gel or slurry is delivered to the skin, and the patch remains in contact with the skin for a period of time sufficient to allow the *Plantago major* extract to be absorbed through the skin into the user's system, resulting in the loss of desire to smoke or chew tobacco. The patch is replaced as needed to maintain the tobacco aversion.

The transdermal patch of the present invention offers significant advantages over prior art nicotine patches and preparations of *Plantago major* extracts. The patch of the present invention does not require the use of toxic and addictive nicotine, which has also been shown to be a skin irritant. The danger of increasing the nicotine addiction inherent in the use of nicotine patches is avoided with this invention. The patch of the present invention may be used conveniently and privately, without the requirement for multiple oral dosing of *Plantago major* extract. The side effects of oral dosing with *Plantago major* extract are also avoided.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. An apparatus for aiding in the cessation of tobacco use, comprising:

a preparation of an ethanolic extract from *Plantago major* in an amount effective to cause an aversion to tobacco, said extract being present in a concentration in the range from about 1% to about 100%; and a transdermal patch having said preparation deposited thereon, said transdermal patch for transdermally delivering said preparation to the skin of the user.

2. The apparatus of claim 1 wherein:

said extract is present in a concentration in the range from about 30% to about 90%.

3. The apparatus of claim 1 wherein:

said preparation comprises a gel.

4. The apparatus of claim 3 wherein:

said gel comprises specially denatured alcohol 40, triethanolamine, Carbomer, methyldibromoglutaronitrile and phenoxyethanol.

5. The apparatus of claim 3 wherein:

said gel further comprises dimethylsulfoxide.

6. The apparatus of claim 3 wherein said transdermal patch comprises:

a permeable, nonreactive inner layer; and a nonpermeable, nonabsorbent outer layer, said gel being disposed between said inner and outer layers.

7. The apparatus of claim 3 wherein said permeable, nonreactive inner layer further comprises an adhesive permeable, nonreactive inner layer.

8. The apparatus of claim 7 wherein said transdermal patch further comprises:

a nonpermeable, nonabsorbent release layer disposed on said adhesive permeable, nonreactive inner layer.

9. A method for aiding in the cessation of tobacco use, comprising the steps of:

applying a transdermal patch having a preparation deposited thereon, said preparation comprising an ethanolic extract from *Plantago major* in an amount effective to cause an aversion to tobacco, said extract being present in a concentration in the range from about 1% to about 100%; and transdermally delivering said preparation to the skin of the user.

10. The method of claim 9 wherein:

said extract is present in a concentration in the range from about 30% to about 90%.

11. A process of preparing a transdermal patch for aiding in the cessation of tobacco use, comprising:

treating a quantity of the herb *Plantago major* to provide an ethanolic extract;

preparing a gel containing said *Plantago major* extract; and incorporating said gel into a transdermal patch.

12. The process of preparing said transdermal patch of claim 11 wherein said step of treating said herb *Plantago major* to provide said extract comprises maceration of said herb *Plantago major*.

13. The process of preparing said transdermal patch of claim 11 wherein said preparing a gel comprises:

(a) adding water to a vessel;

(b) creating a vortex in said water;

(c) adding a gelling agent to said water;

(d) mixing said water and gelling agent until said gelling agent is dissolved;

(e) adding ethanolic extract of *Plantago major* to the dissolved gel and water; and (f) adding a neutralizer to the mixture of extract and dissolved gel.

* * * * *

UNITED STATES PATENT AND TRADEMARK OFFICE
CERTIFICATE OF CORRECTION

Page 1 of 3

PATENT NO. : 5,716,635

DATED : February 10, 1998

INVENTOR(S) : Mary E. Cody

It is certified that error appears in the above-identified patent and that said Letters Patent is hereby corrected as shown below:

Drawings:

The Title page should be deleted and substitute therefor the attached page.

United States Patent [19]

Cody

[11] Patent Number: 5,716,635

[45] Date of Patent: Feb. 10, 1998

[54] PLANTAGO MAJOR TRANSDERMAL PATCH FOR USE IN TREATING A TOBACCO OR NICOTINE HABIT

[75] Inventor: Mary E. Cody, Boonton Township, N.J.

[73] Assignee: M. E. Cody Products, Inc., Boonton Township, N.J.

[21] Appl. No.: 504,014

[22] Filed: Jul. 19, 1995

[51] Int. Cl.$^6$ ................................. A61L 15/16
[52] U.S. Cl. .............. 424/447; 424/195.1; 424/448; 424/449; 514/813
[58] Field of Search ................. 424/448, 449, 424/447, 195.1; 514/813

[56] References Cited

U.S. PATENT DOCUMENTS

| | | | |
|---|---|---|---|
| 4,284,089 | 8/1981 | Ray | 131/270 |
| 4,716,120 | 12/1987 | Tsay et al. | 424/276.1 |
| 4,821,745 | 4/1989 | Rosen et al. | 131/270 |
| 4,839,174 | 6/1989 | Baker et al. | 424/447 |
| 4,908,213 | 3/1990 | Govil et al. | 424/447 |
| 4,920,989 | 5/1990 | Rose et al. | 131/270 |
| 4,943,435 | 7/1990 | Baker et al. | 424/448 |
| 4,946,853 | 8/1990 | Bannon et al. | 514/343 |
| 4,953,572 | 9/1990 | Rose et al. | 131/270 |
| 4,963,356 | 10/1990 | Calenoff et al. | 424/276.1 |
| 5,016,652 | 5/1991 | Rose et al. | 131/270 |
| 5,135,753 | 8/1992 | Baker et al. | 424/435 |
| 5,162,037 | 11/1992 | Whitson-Fischman | 600/12 |
| 5,192,542 | 3/1993 | Hubbs et al. | 424/195.1 |

OTHER PUBLICATIONS

Clinical Study. An Open Label Evaluation of the Tobacco Aversion Caused by Plantago Major Tincture in Subjects Who Are Heavy Smokers. Essex Testing Clinic Inc., Verona, NJ pp. 1–22. Constance J. DiFiglia, M.D., 1992.

Oscar E. Boericke, A.B., M.D., Homoeopathic Materia Medica; pp. 521–522. 1953.

Primary Examiner—D. Gabrielle Phelan
Attorney, Agent, or Firm—Fishman, Dionne, Cantor & Colburn

[57] ABSTRACT

A transdermal patch containing an extract of the herb Plantago major is presented. Use of the transdermal patch, of the present invention, produces a diminished desire for tobacco (i.e., nicotine) without the use of nicotine itself.

13 Claims, 1 Drawing Sheet

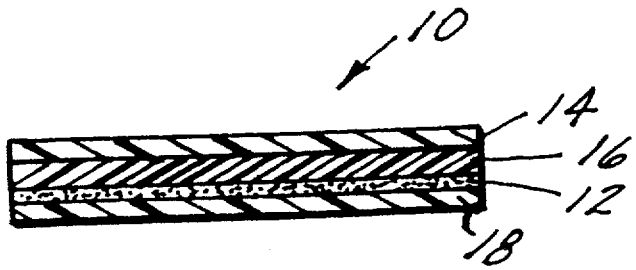

UNITED STATES PATENT AND TRADEMARK OFFICE
CERTIFICATE OF CORRECTION

PATENT NO. : 5,716,635            Page 3 of 3
DATED : February 10, 1998
INVENTOR(S) : Mary E. Cody It is certified that error appears in the above-identified patent and that said Letters Patent is hereby corrected as shown below:

In the drawings, sheet 1, the reference numeral 12 should be applied to the layer which is adjacent release layer 18.
A reference numeral 16 should be applied to the layer which is adjacent layer 12.

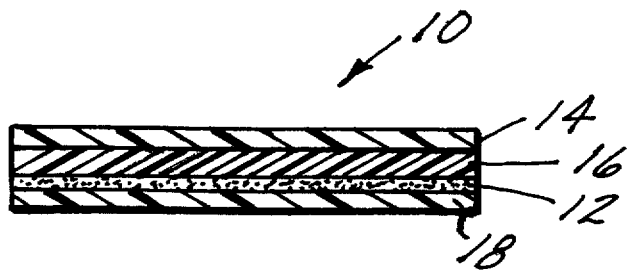

Signed and Sealed this

Eighth Day of September, 1998

*Attest:*

BRUCE LEHMAN

*Attesting Officer*      *Commissioner of Patents and Trademarks*